United States Patent [19]

Nohira

[11] Patent Number: 5,321,154
[45] Date of Patent: Jun. 14, 1994

[54] OPTICAL RESOLUTION OF (±)-2-(4-ISOBUTYLPHENYL)-PROPIONIC ACID

[75] Inventor: Hiroyuki Nohira, Urawa, Japan

[73] Assignee: Nagase & Company, Ltd., Osaka, Japan

[21] Appl. No.: 922,393

[22] Filed: Jul. 31, 1992

[30] Foreign Application Priority Data

Aug. 23, 1991 [JP] Japan .................. 2-237210

[51] Int. Cl.$^5$ .............................................. C07B 57/00
[52] U.S. Cl. .................................... 562/401; 562/402; 562/493; 564/304
[58] Field of Search ................. 562/401, 402, 493

[56] References Cited

U.S. PATENT DOCUMENTS

| | | | |
|---|---|---|---|
| 4,209,638 | 6/1980 | Nicholson et al. | 562/401 |
| 4,723,033 | 2/1988 | Erickson | 560/56 |
| 4,752,417 | 6/1988 | Inoue et al. | 562/401 |
| 4,983,765 | 1/1991 | Lukas et al. | 562/401 |
| 5,015,764 | 5/1991 | Manimaran et al. | 562/401 |

FOREIGN PATENT DOCUMENTS

| | | |
|---|---|---|
| 0311385 | 4/1989 | European Pat. Off. |
| 0423467A2 | 4/1991 | European Pat. Off. |
| 59-152346 | 8/1984 | Japan . |
| 60-228442 | 11/1985 | Japan . |
| 63-227543 | 9/1988 | Japan . |
| 1596033 | 8/1981 | United Kingdom . |

OTHER PUBLICATIONS

Patent Abstracts of Japan, vol. 10, No. 383, Dec. 23, 1986.

*Primary Examiner*—Jose' G. Dees
*Assistant Examiner*—Vera C. Clarke
*Attorney, Agent, or Firm*—Armstrong, Westerman, Hattori, McLeland & Naughton

[57] ABSTRACT

(±)-2-(4-Isobutylphenyl)-propionic acid can be resolved into optically active isomers easily and with high yields. The method is characterized by the use of the optically active amine of the following general formula (I) or (II) as a resolving agent.

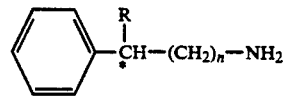

(I)

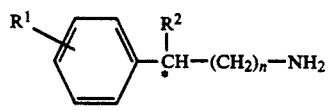

(II)

4 Claims, No Drawings

OPTICAL RESOLUTION OF (±)-2-(4-ISOBUTYLPHENYL)-PROPIONIC ACID

Technical Field

The present invention relates to a method for optical resolution of (±)-2-(4-isobutylphenyl)-propionic acid (a racemic mixture).

Background of the Invention 2-(4-Isobutylphenyl)-propionic acid exhibits anti-inflammatory activity and analgesic/antipyretic activity. The compound is used as a drug a nonproprietary name of ibuprofen.

With regard to the physiological activity of optical isomers of this compound, it has been known that (+)-2-(4-isobutylphenyl)-propionic acid is 160 times stronger than (−)-2-(4-isobutylphenyl)-propionic acid in vitro but, in vivo, there is no significant difference between them because the (−)-isomer is converted into the (+)-isomer with higher pharmacological effect.

Accordingly, in most of cases, the compound is used, at present, as a racemic mixture. In other words, the present situation is that the compound is supplied as a prodrug with an expectation of entire conversion into the (+)-isomer in vivo. Recently, however, it has been found that, when (−)-isomer is converted to (+)-isomer in vivo, thioester of the (−)-isomer which is produced as an intermediate is accumulated in adipose tissues in a form of a mixed triglycerides the same as in the case of metabolism of fatty acids in vivo (Pharmacia, vol.25, page 2069, 1989). In order to eliminate such a side effect and to ensure the safety of the drug, it has been strongly demauded to supply the (+)-isomer only. Consequently, there is now a strong demand for a practical and industrial method of producing optically active 2-(4-isobutylphenyl)-propionic acid, particularly (+)-2-(4-isobutylphenyl)-propionic acid. (Problems to be solved by the Invention)

Methods for the production of optically active 2-(4-isobutylphenyl)-propionic acid which have been known are a method wherein optically active 1-(p-nitrophenyl)-2-aminopropane-1,3-diol is used (German Patent No. 3814887), a method wherein optically active phenylethylamine, quinine, cinchonidine, etc. are used (U.S. Pat. No. 4,983,765), and the like. However, in the above-mentioned methods, there are disadvantages such as that the yield of the optically active ibuprofen is low or that, due to low optical purity, further purifying steps are to be repeated for resulting in desired optical purity.

Means to Solve the Problems

The present inventor has conducted extensive studies for solving the above problems in optical resolution of (±)-2-(4-isobutylphenyl)-propionic acid, accomplished the present invention and achieved the desired objects.

Thus, the present invention relates to a method for optical resolution of (±)-2-(4-isobutylphenyl)propionic acid, characterized in that, an optically active amine of the following general formula (I) or (II) is used as a resolving agent.

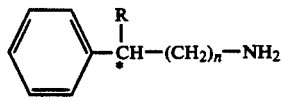

(wherein R is ethyl, n-propyl or isopropyl group; n is 0 or 1; and * is a chiral center)

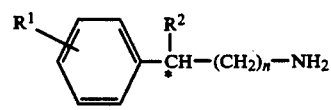

(wherein $R^1$ is bromine, chlorine, lower alkyl or lower alkoxy group; $R^2$ is methyl, ethyl, n-propyl or isopropyl group; n is 0 or 1; and * is a chiral center)

The amines of the above general formulae (I) and (II) used as resolving agents in the present invention are, for example, prepared by a method which is in accordance with that disclosed in Japanese Patent Kokai No. 172853/86.

The characteristic feature of the present invention is that the specific optically active amine of the above general formula (I) or (II) is used as a resolving agent whereby diastereomers of said optically active amine with one of the optically active [i.e. (+)- or (−)- isomer of ] (±)-2-(4-isobutylphenyl)-propionic acid are formed followed by optically resolving wherein the difference in the solubilities are utilized.

There is no particular limitation as to the amount of the optically active amine of the formula (I) or (II) used in the present invention though the use of 0.6–1.2 equivalent of it to one equivalent of (±)-2-(4-isobutylphenyl)-propionic acid is usually preferred in giving the optically active isomer [i.e. (+)- or (−)-isomer] of high purity with high efficiency.

One of the embodiments of the present invention is that (±)-2-(4-isobutylphenyl)-propionic acid and an optically active amine of the general formula (I) or (II) are dissolved in a solvent (selected from a group consisting of water, methanol, ethanol, 2-propanol, acetone, 2-butanone, ethyl acetate, dioxane, hexane, chloroform and a mixture of 2 or more of any of them) with heating, the solution is then cooled to make it supersaturated and, a salt (diastereomer salt) of optically active 2-(4-isobutylphenyl)-propionic acid [i.e. (+)- or (−)-isomer] with the optically active amine of the general formula (I) or (II) is added as seed crystals if necessary whereupon said diastereomer salt is crystalled.

The diastereomer salt is separated and, if necessary, recrystallized. Then it is treated with a base such as sodium hydroxide, potassium hydroxide or ammonium hydroxide and extracted with an organic solvent such as diethyl ether, methylene chloride, chloroform, benzene or toluene so that the optically active amine of the general formula (I) or (II) is recovered.

The mother liquor is then acidified with mineral acid such as hydrochloric acid or sulfuric acid, extracted with organic solvent such as diethyl ether, methylene chloride, chloroform, benzene or toluene and the extract is dried and concentrated to give optically active 2-(4-isobutylphenyl)-propionic acid [i.e. (+)- or (−)-isomer].

EXAMPLES

The present invention will be further illustrated by way of the following examples.

EXAMPLE 1

Optical resolution using an optically active 2-(4-methylphenyl)-3-methylbutylamine (hereinafter referred to as MPBA)

(±)-2-(4-Isobutylphenyl)-propionic acid (hereinafter referred to as IBP) (2.00 g; 10.2 mmoles), 120 g (6.79 mmoles) of (−)-MPBA as measured in methanol of sodium hydroxide were dissolved in 29.5 ml of 95% methanol with heating and the crystals obtained by keeping at 20° C. were filtered to give 1.60 g (4.28 mmoles) of crude salt of (+)-IBP with (−)-MPBA, $[\alpha]_{435}-11.2°$ (c=1, methanol), m.p. 175°-178° C.

The salt was recrystallized from 25 ml of 95% methanol once to give 1.22 g (3.27 mmoles) of pure salt of (+)-IBP with (−)-MPBA, $[\alpha]_{435}-10.1°$ (c=1, methanol, m.p. 186°-189° C. The yield where one half of the used IBP was set 100% was 65.5%.

(−)-MPBA was liberated by adding 5 ml of 1N aqueous solution of sodium hydroxide to the resulting salt and removed by extracting with each 5 ml of diethyl ether twice. The mother liquor was acidified with 2.2 ml of 3N hydrochloric acid and extracted with 10 ml and then with 5 ml of diethyl ether.

The extracts were dried over anhydrous sodium sulfate and concentrated to give 0.56 g (2.85 mmoles) of (+)-IBP as colorless crystals, $[\alpha]_D+56.7°$ (c=1, 99% ethanol), m.p. 50°-51° C. Optical purity was 96.3% and the yield (when one half of the used IBP was set as 100%) was 56.0%. Incidentally, the optical purity was calculated on the basis that $[\alpha]_D+58.9°$ (c=1, 99% ethanol) was set as 100%.

EXAMPLE 2

Optical resolution using (−)-α-tolylethylamine (hereinafter referred to as TEA)

(±)-IBP (206 mg; 1 mmole) and 135 mg (1 mmole) of (−)-TEA were dissolved in 1.0 ml of 95% ethanol with heating and the crystals which were separated out upon cooling were filtered to give 129 mg (0.39 mmole) of salt of (−)-IBP with (−)-TEA. The resulting salt was liberated by the same manner as in Example 1 to give 74 mg (0.38 mmole) of (−)-IBP, $[\alpha]_D-37.5°$ (c=1, 99% ethanol). Optical purity was 63.7% and the yield (on the basis that one half of the used IBP was set as 100%) was 75.5%.

EXAMPLE 3

Optical resolution using (−)-α-ethylbenzylamine (hereinafter referred to as EBA)

(±)-IBP (206 mg; 1 mmole) and 135 mg (1 mmole) of (−)-EBA were dissolved in 1.5 ml of 95% ethanol with heating and the crystals which were separated out upon cooling were filtered to give 116 mg (0.35 mmole) of salt of (+)-IBP with (−)-EBA. The salt i.e. (−)-EBA was liberated by the same manner as in Example 1 to give 68 mg (0.35 mmole) of (+)-IBP, $[\alpha]_D-36.1°$ (c=1, 99% ethanol). Optical purity was 61.3% and the yield (on the basis that one half of the used IBP was set as 100%) was 69%.

EXAMPLE 4

Optical resolution using (+)-3-methyl-2-phenylbutylamine (hereinafter referred to as PBA).

(±)-IBP (0.412 g; 2 mmoles) and 0.326 g (2 mmoles) of (+)-PBA as measured in methanol were dissolved in 3.5 ml of methanol with heating followed by being crystallized at room temperature. The crystals were filtered to give 0.466 g (1.26 mmoles) of crude salt of (−)-IBP with (+)-PBA. This salt was recrystallized from each 2.5 ml of methanol twice to give 0.228 g (0.618 mmole) of pure salt of (−)-IBP with (+)-PBA, $[\alpha]_{435}^{28}+7.9°$ (c=1, 99% ethanol), $[\alpha]_D^{28}+3.5°$ (c=1, 99% ethanol), m.p. 169°-172° C. The yield (on the basis that one half of the used (±)-IBP was set as 100%) was 61.8%.

To the salt was added 1.0 ml of 1N aqueous solution of sodium hydroxide, the liberated (+)-PBA was removed by extracting with diethyl ether, the aqueous layer was made acidic by adding 0.5 ml of 3N hydrochloric acid thereto and extracted with diethyl ether. The ether layer was dried over anhydrous magnesium sulfate and the solvent was evaporated in vacuo to give 0.127 g (0.617 mmole) of (−)-IBP, colorless liquid, $[\alpha]_{435}^{26}-114°$ (c=1, 99% ethanol), $[\alpha]_D^{26}-51.7°$ (c=1, 99% ethanol), optical purity (on the basis that $[\alpha]_D=-59.9°$ (c=1, 99% ethanol) was set as 100%) was 89.4%.

The mother liquor after filtering off the crude salt of (−)-IBP with (+)-PBA was evaporated to dryness in vacuo to give 0.255 g (0.691 mmole) of salt of (+)-IBP with (+)-PBA, $[\alpha]_{435}^{26}+20.7°$ (c=1, 99% ethanol), $[\alpha]_D^{26}+11.0°$ (c=1, 99% ethanol), m.p. 130°-133° C. (+)-PBA was liberated by the same manner as in the case of (−)-IBP.(+)-PBA to give 0.115 g (0.558 mmole) of (+)-IBP, colorless liquid, in 55.8% yield, $[\alpha]_{435}^{25}+90.7°$ (c=1, 99% ethanol), $[\alpha]_D^{26}+42.8°$ (c=1, 99% ethanol), optical purity 72.7%.

EXAMPLE 5

Optical resolution using (−)-3-methyl-2-phenylbutylamine (hereinafter referred to as PBA).

(±)-IBP 0.412, g (2.0 mmoles) and 0.326 g (2.0 mmoles) of (−)-PBA as measured in methanol were dissolved in 7.0 ml of 80% methanol (MeOH/H$_2$O=80/20) with heating, followed by being crystallized at room temperature The crystals were filtered to give 0.330 g of crude salt of (+)-IBP with (−)-PBA. The crude salt was recrystallized from 5.3 ml of 80% methanol to obtain 0.266 g (0.721 mmole) of pure salt of (+)-IBP with (−)-PBA. $[\alpha]_D-9.30°$ (c=1, methanol), m.p. 168°-173° C.

To this salt was added 0.9 ml of 1N aqueous solution of sodium hydroxide, and (−)-PBA was removed by twice extraction with 2 ml of diethyl ether. The aqueous layer was acidified with hydrochloric acid and extracted three times with 2 ml of diethyl ether. The extract was dried over anhydrous magnesium sulfate and the solvent was evaporated to give 0.145 g (0.704 mmole) of (+)-IBP, $[\alpha]_D+56°$ (c=0.9 ethanol), optical purity 95.2%, yield 70.4% (on the basis that one half of the used IBP was set as 100%).

EXAMPLE 6

Optical resolution using (−)-2-(4-chlorophenyl)-3-methylbutylamine (hereinafter referred to as CPBA).

(±)-IBP 0.52 g (2.52 mmoles) and 0.50 g (2.53 mmoles) of (−)-CPBA as measured in methanol were dissolved in 15 ml of 90% methanol (MeOH/H$_2$O=90/10) with heating, followed by being crystallized at room temperature The crystals were filtered to obtain 0.64 g of (+)-IBP.(−)-CPBA crude salt, $[\alpha]_D$−10.6° (c=1, methanol), m.p. 184.5° C.

This crude salt was recrystallized from 15 ml of 90% methanol to give 0.46 g of (+)-IBP.(−)-CPBA salt, $[\alpha]_D$−11.0° (c=1, methanol), m.p. 184.2° C. The resulting salt was recrystallized again from 5 ml of 90% methanol to give pure salt of (+)-IBP with (−)-CPBA, $[\alpha]_D$−10.0° (c=1, methanol), m.p. 188.1° C.

To this pure salt was added 20 ml of 1N aqueous solution of sodium hydroxide, and (−)-CPBA was removed by twice extraction with 10 ml of diethyl ether. The aqueous layer was acidified with hydrochloric acid and extracted two times with 10 ml of diethyl ether. The extract was dried over anhydrous magnesium sulfate and the solvent was evaporated to give 0.11 g of (+)-IBP, $[\alpha]_D$+55.9° (c=1, ethanol), m.p. 48.0° C., optical purity 94.9% (on the basis that $[\alpha]_D$=+58.9° (c=1, ethanol) was set as 100%), yield 42.3% (on the basis that one half of the used IBP was set as 100%).

Comparative Example

Optical resolution using (−)-α-phenethylamine (hereinafter referred to as PEA)

(±)-IBP (9.70 g) and 5.70 g of (−)-PEA were dissolved in 40.0 ml of 95% ethanol with heating and the crystals which were separated out upon cooling were filtered to give a salt of (+)-IBP with (−)-PEA. The salt was recrystallized from 95% ethanol for five times to give 3.29 g of pure salt of (+)-IBP with (−)-PEA, $[\alpha]_{435}$−1.39° (c=1, 99% ethanol). (−)-PEA was liberated by the same manner as in Example 1 to give 2.03 g of (+)-IBP, $[\alpha]_D$50.1° (c=1, 99% ethanol), optical purity 85% and the yield (on the basis that one half of the used IBP was set as 100%) was 42%.

Merit of the Invention

As fully explained hereinabove, when specific optically active amine of the general formula (I) or (II) is used as a resolving agent in accordance with the method of the present invention, any of the desired optically active 2-(4-isobutylphenyl)propionic acid [i.e. (+)- or (−)-isomer] can be easily obtained in high yield starting from (±)-2-(4-isobutylphenyl)-propionic acid.

What we claim is:

1. A method for optically resolving racemic 2-(4-isobutylphenyl)-propionic acid, which comprises reacting the racemic acid with an optically active amine of the formula

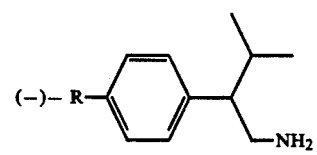

in solution in a solvent;
and separating (+) (−)-diastereomer salt from the solution.

2. A method for optically resolving racemic 2-(4-isobutylphenyl)-propionic acid, which comprises reacting the racemic acid with an optically active amine of the formula

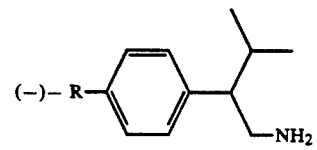

wherein R is chlorine or methyl, in solution in a solvent;
and separating (+) (−)-diastereomer salt from the solution.

3. A method for optically resolving racemic 2-(4-isobutylphenyl)-propionic acid, which comprises reacting the racemic acid with an optically active amine of the formula

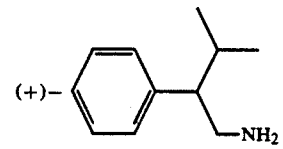

in solution in a solvent;
and separating (−) (+)-diastereomer salt from the solution.

4. A method for optically resolving racemic 2-(4-isobutylphenyl)-propionic acid which comprises reacting the racemic acid with an optically active amine of the formula

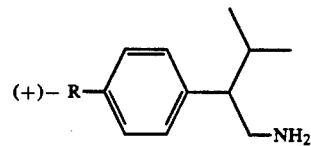

wherein R is chlorine or methyl, in solution in a solvent;
and separating (−)(+)-diastereomer salt from the solution.

* * * * *

UNITED STATES PATENT AND TRADEMARK OFFICE
CERTIFICATE OF CORRECTION

PATENT NO.  : 5,321,154
DATED       : June 14, 1994
INVENTOR(S) : Hiroyuki NOHIRA It is certified that error appears in the above-identified patent and that said Letters Patent is hereby corrected as shown below:

Column 1, line 37, "demauded" should read --demanded--.

Column 3, line 11, "120g" should read --1.20g--.

Column 3, line 12, after "methanol" insert therefor --and 0.12g (2.85 mmoles).

Column 3, line 20, "(c=1, methanol," should read --(c=1, methanol),--.

Column 6, line 5, change

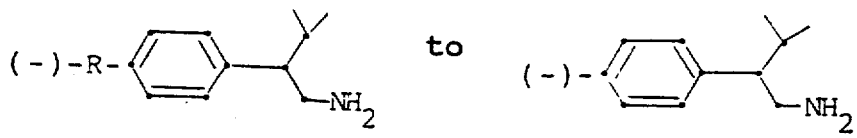 to 

Signed and Sealed this

Fourteenth Day of February, 1995

Attest:

BRUCE LEHMAN

Attesting Officer                Commissioner of Patents and Trademarks